United States Patent
May et al.

(10) Patent No.: US 6,974,322 B2
(45) Date of Patent: Dec. 13, 2005

(54) IMPLANT-SUPPORTED DENTAL PROSTHESIS AND A PROCESS FOR ITS PRODUCTION

(76) Inventors: Dittmar May, Ernst-Becker-Strasse 18, D-44534 Leinen (DE); Pascale Grote, Hanauer Vorstadt 31, D-63450 Hanau (DE); Egbert Kremer, Lübecker Weg 26, D-63454 Hanau (DE); Werner Groll, Gartenstrasse 5, D-63755 Alzenau (DE)

( * ) Notice: Subject to any disclaimer, the term of this patent is extended or adjusted under 35 U.S.C. 154(b) by 194 days.

(21) Appl. No.: 10/193,261

(22) Filed: Jul. 12, 2002

(65) Prior Publication Data

US 2002/0177106 A1    Nov. 28, 2002

Related U.S. Application Data

(63) Continuation of application No. 09/665,951, filed on Sep. 21, 2000, now abandoned.

(30) Foreign Application Priority Data

Sep. 22, 1999  (DE) ................. 199 45 354

(51) Int. Cl.⁷ ................................. A61C 8/00

(52) U.S. Cl. ...................... 433/173; 433/172

(58) Field of Search ................. 433/173, 172, 433/174, 175, 176

(56) References Cited

U.S. PATENT DOCUMENTS

| | | | |
|---|---|---|---|
| 4,516,937 A | 5/1985 | Bosker | 433/173 |
| 4,681,542 A | 7/1987 | Baum | 433/172 |
| 4,850,873 A | 7/1989 | Lazzara et al. | 433/173 |
| 5,006,069 A | 4/1991 | Lazzara et al. | 433/173 |
| 5,078,606 A | 1/1992 | Soderberg | 433/173 |
| 5,259,759 A | 11/1993 | Jorneus et al. | 433/173 |
| 5,674,072 A | 10/1997 | Moser et al. | 433/173 |
| 5,688,123 A | 11/1997 | Meiers et al. | 433/172 |
| 5,803,735 A | 9/1998 | Gittleman | 433/172 |
| 5,882,200 A * | 3/1999 | Sutter et al. | 433/173 |
| 5,888,066 A | 3/1999 | Morgan | 433/173 |
| 6,126,662 A * | 10/2000 | Carmichael et al. | 606/72 |
| 6,155,828 A * | 12/2000 | Lazzara et al. | 433/173 |

FOREIGN PATENT DOCUMENTS

WO       WO99/29255    *  6/1999

* cited by examiner

Primary Examiner—Cary E. O'Connor
(74) Attorney, Agent, or Firm—Smith, Gambrell & Russell LLP

(57) ABSTRACT

An implant-supported dental prosthesis (10) has in its main body (12) several basal recesses (13) in which in each case a conical cap (7) is embedded in self-curing plastic. Each conical cap (7) sits on a conical peg (6) of a construction post (2), which is inserted in a conical hole of an enossal implant (1). Exclusively prefabricated components are used for the production of the dental prosthesis. The embedding of the conical caps (7) in the main body (12) of the dental prosthesis (10) takes place in a single session in the dental practice, after which the dental prosthesis is completed.

11 Claims, 3 Drawing Sheets

IMPLANT-SUPPORTED DENTAL PROSTHESIS AND A PROCESS FOR ITS PRODUCTION

Figure 1:
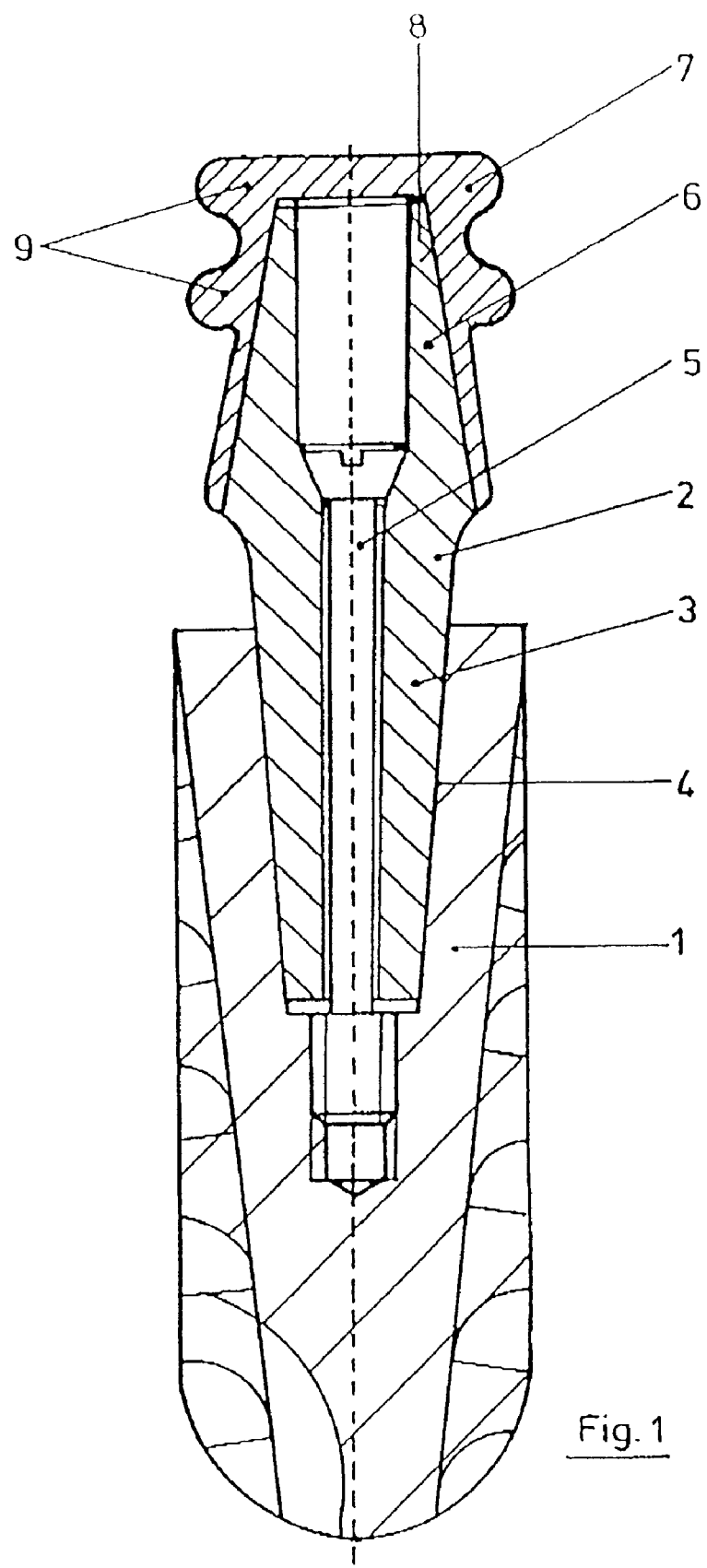

This application is a continuation of U.S. application Ser. No. 09/665,951, filed Sep. 21, 2000, now abandoned.

DESCRIPTION

The invention relates to an implant-supported dental prosthesis with several construction posts in each case accommodated in a conical location hole of an enossal implant, in each case with an occlusal conical peg for connection to the dental prosthesis.

Enossal implants, provided in each case with a construction post, are increasingly employed for anchoring dental prostheses. The use of conical posts which are inserted with a conical section in a positive-locking and frictional manner into a corresponding conical hole of the implant and are secured by means of a central screw (EP 0 707 835 A1) has the advantage over other geometrically interlocked types of connection that a high position stability under load is ensured and a rotational alignment in any desired position is possible. The latter is particularly advantageous in the case of construction posts on which the occlusal construction peg provided for connection with the dental prosthesis is angled. Furthermore, the conical connection between the enossal implant and the construction post is free from gaps and bacteria-tight.

If such construction posts are intended only for stabilizing and holding dental prostheses supported on the mucous membrane, a construction as a magnet anchor or ball anchor is chosen. In both cases, in each case one anchor element is embedded in the prosthesis, enabling a detachable connection to be made with the head of the construction post by means of a magnetic connection or a ball-head connection. However, there is no permanent, load-bearing connection between the dental prosthesis and the construction post with which all the forces arising are supported on the implants via the construction posts.

For the construction of implant-supported dental prostheses, the conical crown technique is a proven method. In this, an occlusal conical peg is provided on each construction post, serving as the force-transmitting connection with the dental prosthesis.

In dental practice, an impression is usually taken, by which the position of all the conical pegs is determined. The dental technician produces an analogous model from this impression in the laboratory. The dental technician models a primary crown in wax on the conical peg and pre-mills it in the corresponding conical angle with the aid of a milling unit. The primary crown is then pegged and embedded; it is cast, removed from the embedding material, blasted and fitted. The primary crown is after-milled and polished. A secondary crown is produced on the primary crown with modelling plastic and wax, in particular as a facing bridge, as caps without retention for gluing in a metal frame or as a cap with retention for incorporating into prostheses. The secondary crown is pegged and embedded; it is cast, removed from the embedding material, blasted and fitted.

This production requires a considerable outlay on work in the dental laboratory and in the dental practice; several visits to the dentist by the patient are necessary.

The object of the invention is therefore to develop an implant-supported dental prosthesis of the above-mentioned type such that it can be processed in a finished form directly in the mouth of the patient without taking impressions, producing models and milling and casting in the dental laboratory.

This object is achieved according to the invention in that several conical caps are embedded in the main body of the dental prosthesis, each of which has a conical hole matching in shape the conical peg assigned to it.

The use of embedded conical caps as connecting elements between the conical pegs of the construction posts and the dental prosthesis enables the dental prosthesis to be completed in a single session with prefabricated components and in particular without taking impressions and producing models beforehand, by joining the conical caps in their position located on the conical pegs with the main body of the prosthesis by conventional techniques, in particular by gluing or polymerizing-in. In particular, the need to model a primary crown on the conical peg of the construction post and to produce and work it is eliminated. As a result, any need to carry out any further work in the dental laboratory after production of the actual dental prosthesis and fitting in the dental practice is eliminated. Any taking of impressions and production of models is eliminated.

By the use of exclusively prefabricated components, the disadvantages and difficulties resulting from the expansion properties of embedding compositions are eliminated. The expensive modelling of primary and secondary components is eliminated, as is the time-consuming development of the secondary components. Casting errors are avoided. With the relatively small amount of materials employed, the amount of consumable materials is likewise reduced. The accuracy of fit achieved is consistently high.

Optimum alignment of the conical peg is achieved by the free positioning of straight and angled construction posts in the conical hole of the implant.

Retention projections which allow an increased anchoring of the conical caps in the main body of the dental prosthesis are preferably provided on the outside of the conical caps. These can be, for example, circumferential bulges.

The invention furthermore relates to a process for the production of an implant-supported dental prosthesis, wherein in each case a construction post which has an occlusal conical peg is inserted into several enossal implants.

The process according to the invention, which is made possible by the use of prefabricated conical caps as connecting elements, is characterized in that in the main body of the dental prosthesis, in the region in each case of a construction peg, a basal recess which has a lateral filling opening is provided, in that on each conical peg of the construction posts in each case a conical cap which matches this is mounted, in that the dental prosthesis is inserted into the mouth such that each conical cap projects into a basal recess, and in that each basal recess is filled with self-curing plastic through the lateral filling opening, and after curing thereof the dental prosthesis is removed and finished.

The prepared dental prosthesis is therefore inserted and completed in a single session in the dental practice exclusively using prefabricated components, without further working steps in the dental laboratory being necessary. The patient can therefore leave the dental practice with the completed dental prosthesis directly after insertion of the dental prosthesis.

Figure 5:
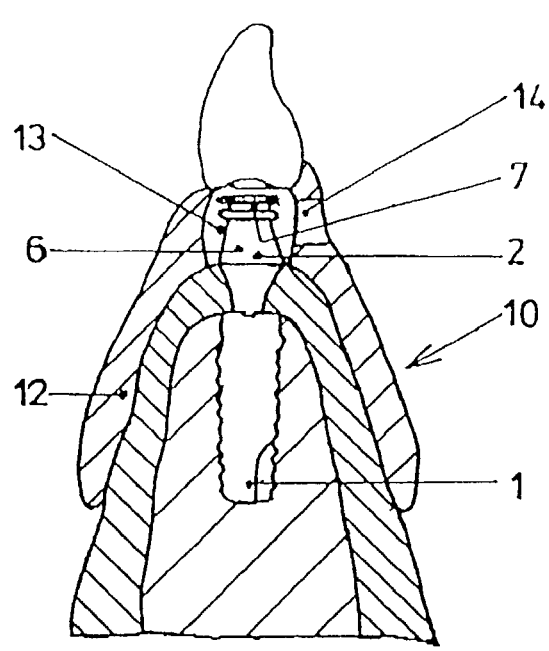
Figure 6:
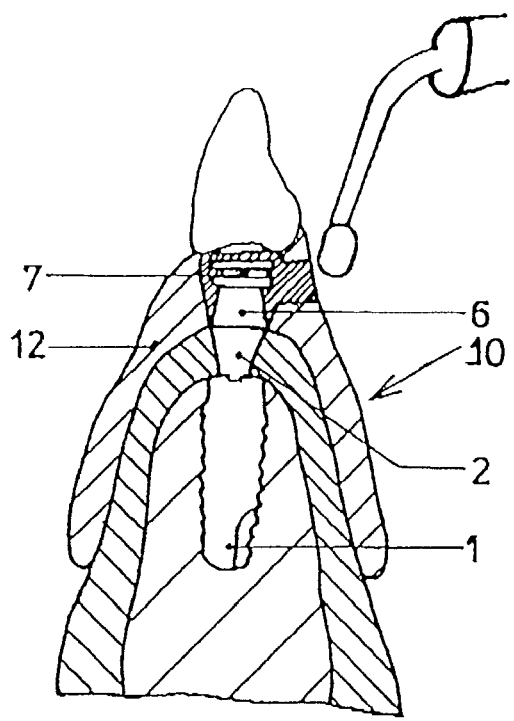
Figure 7:
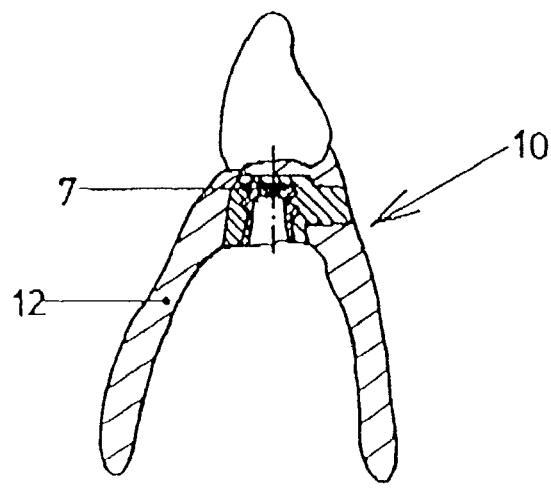

An embodiment example of the invention shown in the drawing is described in more detail below. In the drawing:

FIG. 1 shows in a longitudinal section a construction post which is inserted in an implant and carries a conical cap, FIGS. 2–6 show in each case in a vertical section successive steps in the production of an implant-supported dental prosthesis and FIG. 7 shows the completed dental prosthesis, also in a vertical section.

FIG. 1 shows an enossal implant 1 which is intended to be screwed into a prepared threaded hole in a jaw bone. After the implant 1 has been introduced and has healed in, a construction post 2 with a conical peg 3 on the implant side is inserted into a corresponding conical hole 4 of the implant 1 and secured by means of a central screw 5.

The construction post 2 has a conical peg 6 on its occlusal end projecting out of the implant 1. In the completed state, i.e. after connecting to the dental prosthesis, the conical peg 6 carries a conical cap 7, which has a conical hole 8, which matches in respect of its shape, in particular its diameter and the angle of taper, the conical peg 6. The angle of taper of the conical peg 6 and of the conical hole 8 is preferably in the range from 4° to 8° and is, for example, about 6°.

On its outside the conical cap 7 has circumferential bulges 9 as retention projections which serve to anchor the conical cap after its embedding in plastic.

FIGS. 2–6 show successive processing steps in the production of a dental prosthesis 10, which is shown in its completed state in FIG. 7.

Figure 2:
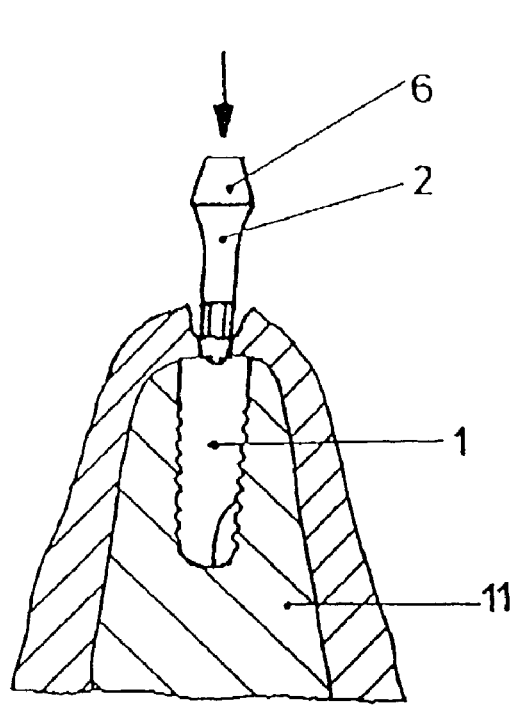

FIG. 2 shows an enossal implant 1, as shown in FIG. 1, inserted in a jaw bone 11. The construction post 2 is inserted into the implant and fixed. While a straight, i.e. not angled, construction post 2 can be fixed directly in any desired rotational position, an angled construction post (not shown) is first aligned in an optimum manner in respect of the given insertion direction and then fixed in this rotational position.

Figure 3:
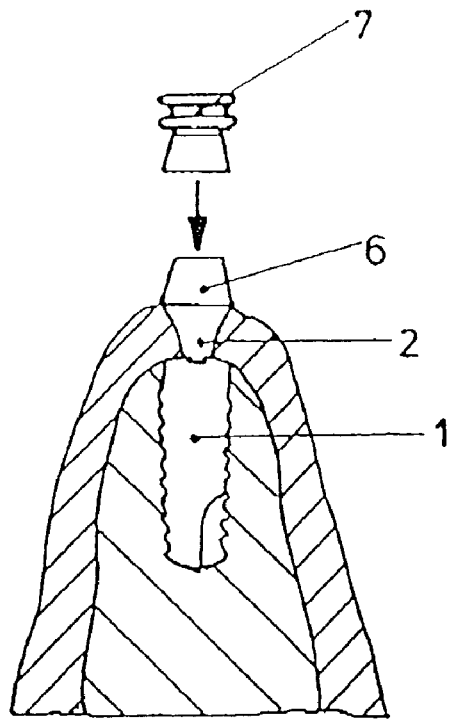
Figure 4:
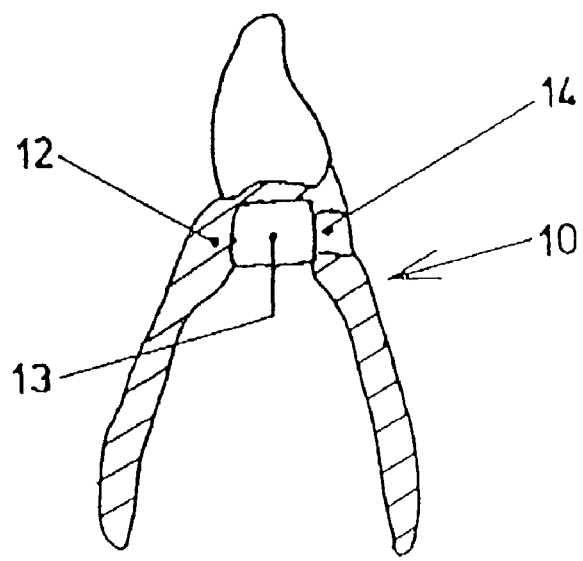

The conical cap 7 is then mounted on the conical peg 6 of the construction post 2 (FIG. 3).

On the prefabricated (or already existing) dental prosthesis 10 (FIG. 4), a basal recess 13 is produced, for example by grinding out, on its main body 12 in each case at the points where there are implants 1 in the jaw. The basal recess 13, which is larger on all sides than the conical cap 7 to be accommodated, is provided with a lateral filling opening 14, which is preferably ground out from the lingual direction.

The dental prosthesis 10 prepared in this way is mounted on the jaw in the arrangement shown in FIG. 5 such that the conical caps 7 are in each case in a basal recess 13. The conical caps 7 are then fixed in the main body 12 of the dental prosthesis 10 with self-curing plastic, which is introduced through the filling openings 14 (FIG. 6). After curing of the plastic, the dental prosthesis 10 is removed from the mouth of the patient and finished in the region of the basal opening and the filling opening 14. The conical caps 7 are fixed in their final situation and position in the dental prosthesis 10. This on the one hand ensures that all the conical caps 7 are aligned in respect of their position and alignment, in particular also in respect of their mutual separation, exactly to the conical pegs 6, anchored in the jaw of the patient, of all the implants. On the other hand, such a stable anchoring of the conical caps in the main body 12 of the dental prosthesis 7 is ensured that complete, force-transmitting support of the dental prosthesis on the jaw is ensured.

What is claimed is:

1. Implant-supported dental prosthesis, comprising:
   several construction posts with each accommodated in a corresponding conical location hole of an enossal implant and a corresponding occlusal conical peg for connection to the dental prosthesis, said occlusal conical peg secured by a central screw that is in communication with said occlusal conical peg and said enossal implant, and
   several conical caps, each conical cap having a conical hole matching in shape with the corresponding occlusal conical peg,
   wherein the dental prosthesis has a lateral filling hole for inserting a self-curing plastic in a space between a basal recess of the dental prosthesis and the conical cap via which the conical cap is connected to the dental prosthesis.

2. Implant-supported dental prosthesis according to claim 1, wherein the conical cap has retention projections on its outside.

3. Implant-supported dental prosthesis according to claim 2, wherein the retention projections are circumferential bulges.

4. Process for the production of an implant-supported dental prosthesis according to claim 1, wherein in each case a construction post which has an occlusal conical peg is inserted into several enossal implants, wherein in a main body of the dental prosthesis, in the region in each case of a construction peg, a basal recess which has a lateral filling opening is provided, in that on each conical peg of the construction posts in each case a conical cap which matches this is mounted, in that the dental prosthesis is inserted into the mouth such that each conical cap projects into a basal recess, and in that each basal recess is filled with self-curing plastic through the lateral filing opening, and after curing thereof the dental prosthesis is removed and finished.

5. An implant-supported prefabricated dental prosthesis shaped to fit in the mouth of a patient in need thereof and to accommodate a plurality of construction posts each of which to be located in a conical location hole of an enossal implant each of said construction posts is secured by means of a central screw, each of said construction posts having a conical shaped lower end on an implant side which is inserted into said corresponding conical location hole of said enossal implant, said dental prosthesis being fitted with a plurality of embedded conical caps each of which caps have a conical hole matching in shape to a conical shaped upper end of a matching construction post with an angle of taper in the range from 4° to 8°, said conical cap is frictionally secured to said each of upper end of said construction posts, said conical cap including at least one retention projection on its outside which serves to anchor said conical cap in a respective basal recess in a main body of the prefabricated dental prosthesis by self-curing plastic, and said prefabricated dental prosthesis having a lateral filling opening for said self-curing plastic.

6. The implant-supported prefabricated dental prosthesis according to claim 5, wherein said retention projection is a circumferential bulge.

7. Process for the production of an implant-supported prefabricated dental prosthesis according to claim 5, wherein a construction post which has an occlusal conical upper end peg is inserted into each of a plurality of enossal implants in the mouth of a patient in need thereof, placing said dental prosthesis, in mating engagement with said conical upper end of said construction post, said prosthesis having a plurality of basal recesses, wherein each basal recess has a filling opening, wherein said filling opening is a lateral opening; and the conical peg of said construction post having mounted thereon a conical cap which matches said conical peg, so that when the prefabricated dental prosthesis is inserted into the mouth of the patient each conical cap projects into its respective basal recess, and then each basal recess is filled with self-curing plastic through the filling opening, curing said plastic; and thereafter removing said dental prosthesis for further finishing.

8. An implant-supported dental prosthesis, comprising:
   at least one construction post with each construction post accommodated in a corresponding conical location hole of an enossal implant and a corresponding occlusal conical peg for connection to the dental prosthesis, said occlusal conical peg secured by a central screw that is in communication with said occlusal conical peg and said enossal implant, and at least one conical cap, each conical cap having a conical hole matching in shape with the corresponding occlusal conical peg,
   wherein the dental prosthesis has a lateral filling hole for inserting a self-curing plastic in a space between a basal recess of the dental prosthesis and the conical cap via which the conical cap is connected to the dental prosthesis.

9. The implant-supported dental prosthesis according to claim 8, wherein the conical cap has retention projections on its outside.

10. The implant-supported dental prosthesis according to claim 9, wherein the retention projections are circumferential bulges.

11. A process for the production of an implant-supported dental prosthesis according to claim 8, comprising:
   inserting a construction post which has an occlusal conical peg into at least one enossal implant, wherein in a main body of the dental prosthesis, in a region of a construction peg, a basal recess which has a lateral filling opening is provided,
   mounting a matching conical cap on each conical peg,
   inserting the dental prosthesis into a mouth into which the prosthesis is to be implanted such that each conical cap projects into a basal recess,
   filling each basal recess with self-curing plastic through the lateral filing opening, removing the dental prosthesis from said mouth after curing thereof, and
   finishing the dental prosthesis.

* * * * *